United States Patent [19]

Cohen et al.

[11] Patent Number: 5,276,019
[45] Date of Patent: Jan. 4, 1994

[54] INHIBITORS FOR REPLICATION OF RETROVIRUSES AND FOR THE EXPRESSION OF ONCOGENE PRODUCTS

[75] Inventors: Jack S. Cohen; Len Neckers, both of Bethesda; Cy Stein, Gaithersburg; Shee L. Loke, Wheaton, all of Md.; Kazuo Shinozuka, Kazo, Japan

[73] Assignee: The United States of America as represented by the Department of Health and Human Services, Washington, D.C.

[21] Appl. No.: 159,017

[22] Filed: Feb. 22, 1988

Related U.S. Application Data

[63] Continuation-in-part of Ser. No. 30,073, Mar. 25, 1987, abandoned.

[51] Int. Cl.$^5$ .................... A61K 31/70; C07H 17/00
[52] U.S. Cl. .................................. 514/44; 536/24.5; 536/23.72
[58] Field of Search ............... 514/44, 47, 48, 51; 536/27, 28, 29

[56] References Cited

U.S. PATENT DOCUMENTS

| | | | |
|---|---|---|---|
| 3,687,808 | 8/1972 | Merigan, Jr. et al. | 435/91 |
| 4,469,863 | 9/1984 | Ts'o et al. | 536/27 |
| 4,511,713 | 4/1985 | Miller et al. | 536/27 |

FOREIGN PATENT DOCUMENTS

61-12215  1/1986  Japan ........................... A01F 12/32

OTHER PUBLICATIONS

Yarchoan et al., Scientific American, vol. 259, pp. 110–119 (1988).
Matsukura et al, Proc. Natl. Acad. Sci., vol. 86, pp. 4244–4248 (1989).
Woolf et al, Nucleic Acids Research, vol. 18, pp. 1763–1769 (1990).
Leiter et al, Proc. Natl. Acad. Sci., vol. 87, pp. 3430–3434 (1990).
Manson et al, Lymphokine Research, vol. 9, pp. 35–42 (1990).
McManaway et al, Lancet, vol. 335, pp. 808–811 (Apr. 7, 1990).
Sankar et al, Eur. J. Biochem., vol. 184, pp. 39–45 (1989).
Agrawal et al, Proc Natl. Acad. Sci., vol. 86, pp. 7790–7794 (1989).
Lennette, Laboratory Diagnosis of Viral Infections, pp. 47–48 (Marcel Dekker, New York, 1985).
Mitsuya et al, Proc. Natl. Acad. Sci., vol. 82, pp. 7096–7100 (1985).
Yarchoan et al, Lancet, pp. 575–580 (Mar. 15, 1986).
Broder, editor, AIDS: Modern Concepts and Therapeutic Challenges, chapters 18 and 19 (Marcel Dekker, New York, 1987).
Stringfellow, editor, Interferon and Interferon Inducers, chapters 7 and 10 (Marcel Dekker, New York, 1980).
J. Amer. Chem. Soc. 106: 6077 (1984).
J. Biochem. Biophys. Methods 13: 97–102 (1986).
Biochem. Biophys. Res. Comm. 140 (2): 735–742.
Cancer Research 45 (9): 4677s–4684s (1985).
J. Chromatography 326: 263–280 (1985).
Nucleic Acids Research 14 (22): 9081–9093 (1986).
J. Org. Chem. 49: 2314–2317 (1984).
J. Org. Chem. 50 (20): 3908–3914 (1985).
Proc. Natl. Acad. Sci. USA 83: 2787–2791 (1986).
Proc. Natl. Acad. Sci. USA 83: 4143–4146 (1986).
Proc. Natl. Acad. Sci. USA 84: 7706–7710 (1987).
Proceedings of the NATO Advanced Study Institute on Targets for the Design of Antiviral Agents, 1984, 259–285.
Tetahedron Letters 23: (41) 4289–4292 (1982).

*Primary Examiner*—John W. Rollins
*Attorney, Agent, or Firm*—James C. Haight; Thomas Ferris; Julie Parker

[57] ABSTRACT

Phosphorothioate oligodeoxyribonucleotide analogs can be used to prevent replication of foreign nucleic acids in the presence of normal living cells, as well as to inhibit the proliferation of neoplastic cells.

43 Claims, 7 Drawing Sheets

ANTI-SENSE: ODN-1: 5'-TCG TCG CTG TCT CC-3'
N-Me-ODN-1: 5'-TCG T*CG CTG T*CT CC-3'
(*DENOTES N3-METHYL-THYMIDINE)

ODN-3: 5'-CAT AGG AGA TGC CT-3'
ODN-2: 5'-GGA GAC AGC GAC GA-3'
ODN-4: 5'-CTG GTT CGT CTC CC-3'

SENSE:
RANDOM: dCn: 5'-(dC)n -3'
dAn: 5'-(dA)n -3'

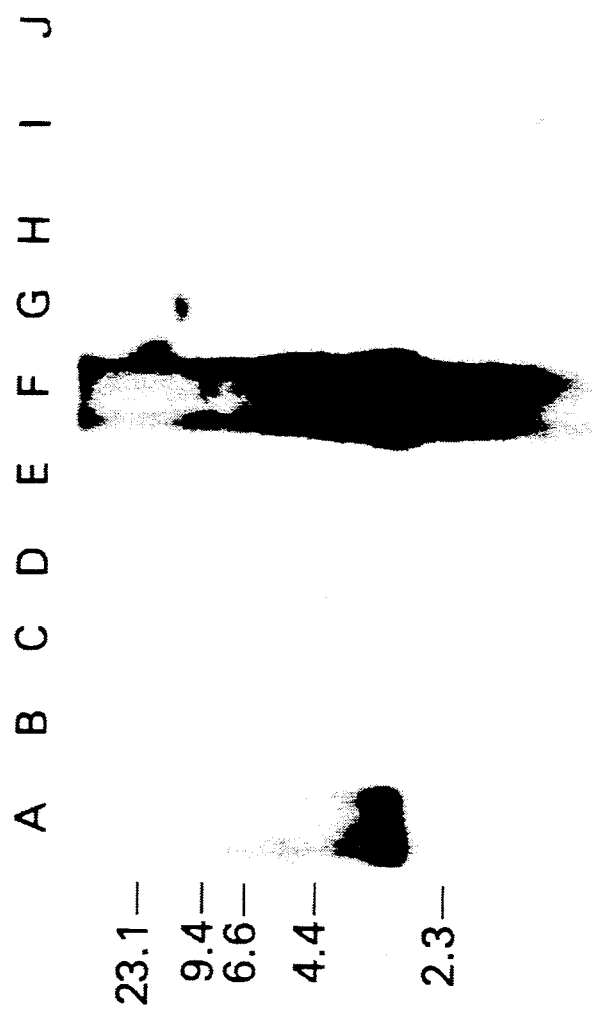

INHIBITORS FOR REPLICATION OF RETROVIRUSES AND FOR THE EXPRESSION OF ONCOGENE PRODUCTS

The present application is a continuation-in-part of Ser. No. 030,073, filed Mar. 25, 1987, now abandoned, the contents of which are incorporated herein by reference.

FIELD OF THE INVENTION

The present invention relates to the inhibition of replication of retroviruses, and is directed more particularly to phosphorothioate oligodeoxyribonucleotide analogs that can be used to prevent replication of foreign nucleic acids in the presence of normal living cells, as well as to inhibit the proliferation of neoplastic cells.

BACKGROUND OF THE INVENTION

Oligodeoxynucleotides, which are complementary to certain gene messages or viral sequences, are referred to as "anti-sense" compounds. These compounds have also been reported to have inhibitory effects against Rous sarcoma virus and human T-cell lymphotropic virus type III (HTLV-III), now called Human Immunodeficiency Virus (HIV). However, the susceptibility of the phosphodiester linkage in normal oligodeoxynucleotides to degradation by nucleases would be expected to reduce their potency and in vivo persistence as antiviral agents.

Methylphosphonate-oligodeoxynucleotide analogs are resistant to nucleases, and because they are uncharged have increased hydrophobicity, which reportedly confers increased cell membrane permeability upon these compounds. The methylphosphonate-oligodeoxynucleotides have been found to exhibit antiviral activity, but these compounds may require high concentrations, typically 100-300 micromoles, in order to elicit strong antiviral effects.

A number of investigators have studied the inhibitory properties of both normal oligodeoxynucleotides and analogs of oligodeoxynucleotides. T'so and coworkers evaluated ethyl phosphotriester and methylphosphonate analogs of oligodeoxynucleotides as nonionic compounds that penetrate cells, and are relatively resistant to degradation by nucleases (cf. U.S. Pat. No. 4,469,863). The ethyl compounds were found, however, to have the disadvantage of undergoing degradative de-ethylation in cells. The methylphosphonates were found to be more stable and to have antiviral activity.

The methylphosphonate analogs as described above have been said to inhibit expression of some genes. However, these compounds have a number of serious disadvantages:

(1) Such compounds are very sensitive to base-catalyzed hydrolysis, making them relatively difficult to synthesize on a routine basis, as compared to poly-anionic oligodeoxynucleotides;

(2) The compounds have relatively low solubility in aqueous media, thus restricting their potential biological/chemotherapeutical usage, as compared to poly-anionic oligodeoxynucleotides;

(3) Relatively high concentrations of these compounds appear to be required to elicit antiviral activity; and (4) There is poor hybridization because of the steric effect of the methyl group.

These factors taken together make chemotherapy impractical in humans with these compounds.

Early work by Zamecnik and co-workers used normal unmodified oligodeoxynucleotides, as well as 3'-end-blocked (2',3'-dideoxyribosyl) analogs of oligodeoxynucleotides, to inhibit the transforming ability, replication and translation of Rous sarcoma virus in vitro. This approach has been extended by both Zamecnik et al. in PNAS, U.S.A., 83:4143-4146 (1986), who studied the inhibition of HIV virus in cultured human cells, and Wickstrom et al., in J. Biochem, Biophys. Methods, 13:97-102 (1986), who investigated the inhibition of the translation of mRNA from vesicular stomatitus virus.

Compared to the aforementioned methylphosphonate analogs, the unmodified, or "O", oligodeoxynucleotides offer the advantages of cost-effectiveness and synthetic accessibility, and moreover appear to have the added advantage of lower effective dosages. However, these unmodified oligodeoxynucleotides are susceptible to degradation by nucleases, even with the inclusion of a 3'-end-blocking residue. Consequently, the use of these compounds in vitro is significantly restricted, and it is highly unlikely that they can be successful in vivo.

The finding that human T-cell lymphotropic virus type III (HTLV-III), hereinafter referred to as Human Immunodeficiency Virus (HIV), is the causative agent of acquired immune deficiency syndrome (AIDS), prompted considerable interest in the development of chemotherapeutic approaches to the treatment of AIDS. A variety of compounds have been reported to have in vitro activity against HIV, although none of these compounds is known to inhibit the expression of the integrated viral genome.

The phosphorothioate oligodeoxynucleotides of several sequences, including sense, anti-sense, nonsense, and homo-oligomers, have been found to inhibit HIV, so that the mechanism of inhibition was unclear. Subsequent work has indicated that the inhibition by homo-oligomers, not complementary to any known sequence in the HIV genome, results from interaction and interference with the function of reverse transcriptase of HIV at low concentrations, i.e. less than 10 micromoles. The mechanism initially expected for complementary base sequence inhibition, known as "translation arrest" of the corresponding mRNA, is apparently not operative in the retrovirus until much higher concentrations of the phosphorothioate compounds are reached, i.e., greater than 25 micromoles. This explains the lack of sequence specificity observed for this inhibitory process.

Attempts have previously been made to inhibit proliferation of normal lymphocytes and HL60 cells using a normal oligodeoxynucleotide (ODN) sequence complementary to a region near the initiation codon of the c-myc gene. Although these results were encouraging, they demonstrated that normal anti-sense c-myc ODNs, even at concentrations as high as 100 micromoles, are not suitable for prolonged inhibition of c-myc protein expression in HL60 cells, even though these normal oligodeoxynucleotides were capable of preventing normal lymphocyte proliferation and c-myc protein expression. It would appear that these insufficiencies of the normal oligodeoxynucleotides, lack of prolonged inhibitory effect and high concentrations required even for short-term effectiveness, were due to enzymatic hydrolysis during the course of the experiment.

Heikkila et al., in *Nature*, 328, Jul. 30 1987, pp. 445-449, disclose that a c-myc oligodexoynucleotide inhibits entry into the S phase in lymphocyte mitogenesis. Small antisense oligomers were added to bulk cell cultures. A pentadecadeoxyribonucleotide complementary to the initiation codon and four downstream codons of human c-myc RNA inhibits mitogen-induced c-myc protein expression in human T-lymphocytes and prevents S phase entry.

MATERIAL INFORMATION DISCLOSURE

Japanese 61 12215 (1983) relates to a method of inhibition of tumor cell growth using oligo DNA.

Merigan, et al. U.S. Pat. No. 3,687,808, concerns the synthesis of synthetic polynucleotides including thioates.

Miller et al. U.S. Pat. No. 4,511,713, concerns inhibiting the replication of foreign nuclei acid with an alkyl or aryl oligonucletide phosphonate complementary to the indicated sequence of the foreign nuclei acid.

Stec, et al., *J. Org. Chem.*, 50(20):3908-3913, 1985, relates to automatic synthesis of phosphorothioates.

Stec, et al., *J. of Chromatography*, 326:263-280, 1985; and LaPlanche, et al., Nuclei Acids Research, 14(22):9081-9093, 1986, are related to the preferred present compounds. Stec refers to phosphorothioate analogues of oligodeoxyribonucleotides and LaPlanche concerns phosphorothioate-modified oligodeoxyribonucleotides.

C. C. Smith et al., *PNAS, U.S.A.*, 83:2787-2791 (May 1986), relate to antiviral effect of an oligo (nucleoside methylphosphonate) complementary to the splice junction of Herpes Simplex Virus Type I. 5 Zamecnik et al., *PNAS, U.S.A.*, 83:4143-4146 (June 1986), concern inhibition of replication of HTLV-III by exogenous synthetic normal oligonucleotides complementary to viral RNA.

Stec et al., in *J. Am. Chem. Soc.* 106: 6077, 1984, have synthesized phosphorothioate oligodeoxynucleotides analogs.

Broder et al., *Proc. Natl. Acad. Sci. U.S.A.* 84: 7706-7710, 1987.

SUMMARY OF THE INVENTION

It is an object of the present invention to overcome deficiencies in the prior art, such as those noted above.

It is another object of the present invention to provide compounds which are effective antiviral agents against retroviruses.

It is yet another object of the present invention to provide compounds which are effective antiviral agents against HIV in human T-cells.

It is a further object of the present invention to inhibit the expression of oncogene product and bring about cessation of cell growth; and still a further object to provide compounds which effect this result.

It is yet a further object of the present invention to inhibit the proliferation of neoplastic cells; and yet another object to provide compounds which can be used as specific treatments to effect this result.

Phosphorothioates are compounds in which one of the non-bridging oxygen atoms in the phosphate portion of the nucleotide is replaced by sulfur. These phosphorothioates have several properties that make them potentially advantageous anti-retroviral analogs. These compounds are stable to cleavage by nucleases, and, since they have the same number of charges as normal oligodeoxynucleotides, have good aqueous solubility.

These compounds also exhibit more efficient hybridization with a complementary DNA sequence than the corresponding methylphosphonate analogs.

The compounds for use in the present invention have the following formula:

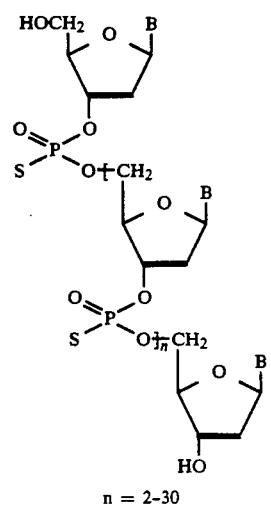

Formula I n = 2-30

It has also been found that the phosphorothioate deoxynucleotides can be combined with normal deoxynucleotides in the same manner as a block copolymer in order to inhibit the proliferation of oncogenes. Alternatively, the phosphorothioate deoxynucleotides can be combined with normal deoxynucleotides in compounds analogous to graft copolymers, wherein the phosphorothioate derivatives are at either end of the chain, with the normal deoxynucleotides on the inside of the chain.

Thus, when R' signifies the phosphorothionate deoxynucleotide group and R2 signifies the normal deoxynucleotide group, the compounds can for example, have the following formulas:

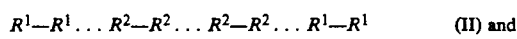

(II) and

(III)

The compounds of the present invention have been found to inhibit HIV and HL-60 cell growth at rather low concentrations, approximately 1-20 micromoles in vitro. In vivo, it is preferred to attain a concentration of the active ingredient of from about 0.1 micromole to about 100 micromoles/cl in blood. This concentration can be achieved in a variety of dosage methods, which will be described hereinafter.

When the compounds of the present invention are in the form of copolymers rather than homopolymers, they can be described by the following formula:

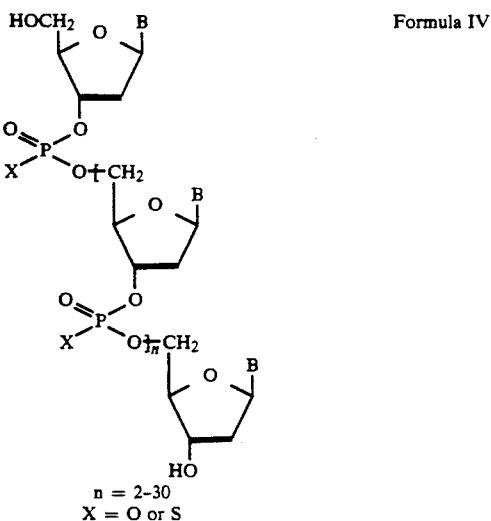

Formula IV n = 2-30
X = O or S

The method of Stec et al., in *J. Org. Chem*, 50 (20):3908–3913 (1985), for automated synthesis of phorphorothioate oligodeoxynucleotides, provides a convenient method for synthesizing the desired compounds. Alternatively, Merigan et al., in U.S. Pat. No. 3,687,808, discloses an alternate method for preparing the thioate esters. However, neither of these methods are efficient enough to permit routine synthesis of sufficient quantities of these compounds for genetic studies.

The oligodeoxynucleotides of the present invention have been found to inhibit expression of the integrated viral genome. The phosphorothioate oligodeoxynucleotides of the present invention have suitable chemical characteristics, namely, the ability to hybridize with complementary DNA/mRNA under physiological conditions, and better solubility properties relative to methylphosphonates. Moreover, the thioesters are as soluble in biological media as the parent compounds. Monitoring the 31P NMR spectra of the ODN-1 sequence, both as unmodified and as a phosphorothioate analog, it was found that the unmodified oligodexoynucleotide had a half-life of about 17 hours, whereas the phosphorothioate bonds were still intact after 10 days, within the accuracy of the 31P NMR measurement (less than 5% decomposition based on the total signal intensity).

BRIEF DESCRIPTION OF THE DRAWINGS

FIG. 8 shows the inhibition of de novo HIV DNA synthesis in ATH8 cells exposed to the virus by 28-mer of oligodeoxycytidine phosphorothioate.

FIGS. 9A-9D show the synergistic enhancement of antiviral activity of 2',3'-dideoxyadenosine with S-dC14.

DETAILED DESCRIPTION OF THE EMBODIMENTS

Figure 1A:
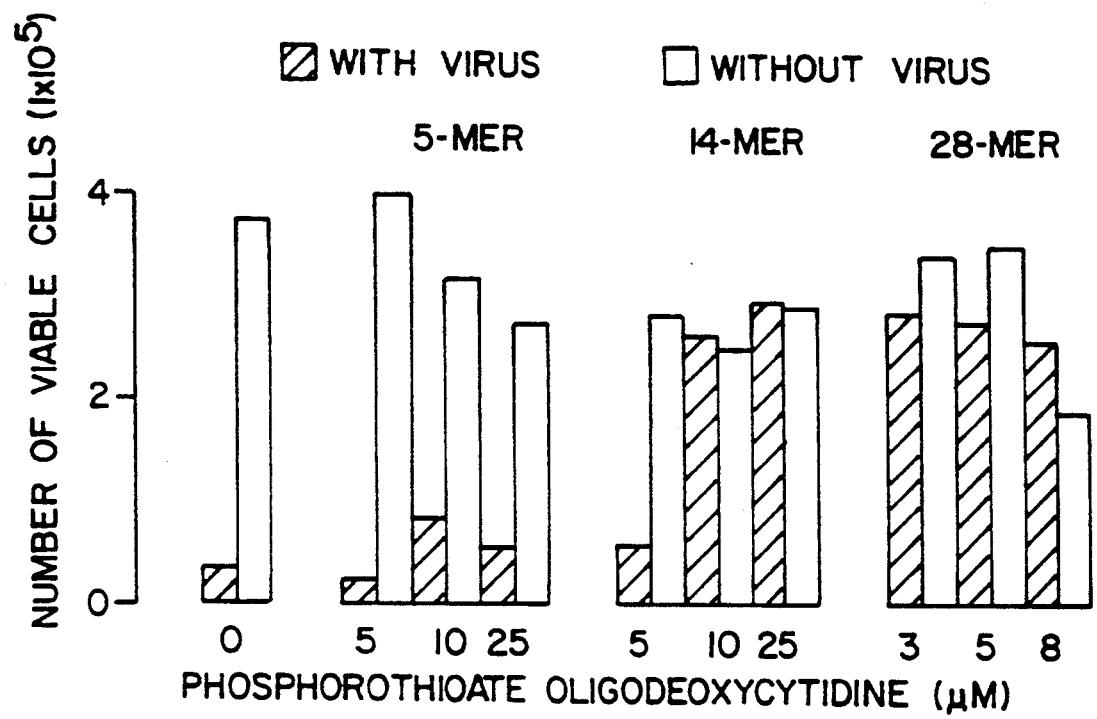
FIGS. 1A-1B show a comparison of anti-HTLV-III activity in three lengths of olgo-dC-S and oligo-dA-S.

The normal oligodeoxynucleotides, methylphosphonate oligodeoxynucleotides, and phosphorothioate oligodeoxynucleotides can be synthesized by either the standard solution procedures or by modification of the procedure of Stec et al. in *J. Am. Chem. Soc.* 106, 6077–6089 (1984) using an automated synthesizer, such as an Applied Biosystems Inc., Model 380-B by the phosphoroamidite method.

Purification of the compounds was performed by reverse phase high performance liquid chromatography. The presence of P-S bonds in the phosphorothioates was shown using 31P NMR spectroscopy. N3-methylthymidine was prepared and converted to the protected phosphoroamidite form and incorporated into the oligomer synthesis.

The phosphorothioates of the present invention can be synthesized in an Applied Biosystems 380-B DNA Synthesizer in a manner similar to that of the synthesis cycle for normal phosphate oligonucleotides using O-methylphosphoramidite. The major difference is in the reagents used during the oxidation step.

A 5% sulfur solution consisting of 7.5 grams of S8 elemental sulfur, dissolved first in 71 ml carbon disulfide along with 71 ml pyridine and 7.5 ml triethylamine, is used as the oxidizing reagent. This reagent occupies bottle #13 on the 380B synthesizer. The total volume given is sufficient for a 3 column synthesis of a 30 mer.

Before and after the oxidation step, the column is washed repeatedly with a 1:1 solution of carbon disulfide and pyridine in bottle #16 position to remove any residual sulfur which might precipitate in the lines. For a three column synthesis of a 30 mer, a total volume of 380 mls of this solution should be sufficient.

The solutions used must be as anhydrous as possible, and should be remade for each new synthesis.

The sulfur oxidation is not as rapid as the iodine oxidation, and thus requires a wait step of 450 seconds during the synthesis cycle, as compared to 30 seconds for the iodine oxidation wait step. Additionally, the end procedure is slightly altered in that the reverse flush is held five seconds longer than normal for a total of ten seconds to ensure the removal of any resulting salts dissolved in methanol after thiophenol is delivered to the column. Of course, variations are possible and will be apparent to those of normal skill in the art without more than routine experimentation.

Oligodeoxynucleotides with blocks of phosphorothioates at the 3' or 5' ends were synthesized by automatically changing the oxidation cycle at the required point. After cleavage from the column and deblocking in aqueous ammonia (60°, 10 h), phosphorothioate oligomers and block copolymers were purified via reverse phase HPLC (PRP-1 column, 1% triethylammonium acetate buffer, pH 7-acetonitrile (20%, increase to 40% at 20 minutes), and the solution was extracted with two equal volumes of ethyl acetate, frozen in dry ice, and lyophilized. The solids were dissolved in 0.3 ml of aM NaCl, and the product was precipitated by the addition of 3.5 volumes of absolute ethanol. The acetate salts of some phosphorothioate oligomers, particularly the homopolymer $dC_{28}$, are extremely insoluble in 1M NaCl. Introduction of a small amount of ammonia vapor, not aqueous ammonia, by a Pasteur pipette solubilized all the solids. The yield determined from absorbance at lambda max was about 30%.

The anti-sense sequence and the control sense and non-sense (same composition as anti-sense but in random sequence) are shown below:

*Anti-sense:* 5'-AAC GTT GAG GGG CAT

*Non-sense:* 5'-CTG AAG TGG CAT GAG

These compounds were purified using high performance liquid chromatography and precipitation by ethanol.

For the biological tests described below, a sequence (S-ODN-1), the phosphorothioate oligodeoxynucleotide was selected which is an anti-sense counterpart to the nucleotide sequence existing in tat-III and art/trs genes of HIV, as these genes are essential for viral replication. This anti-sense oligodeoxynucleotide can block the expression of tat-III and art/trs genes. A sequence (S-ODN-2) was selected, which is complementary to the sequence at the initiation site of tat-III. Additional "random" sequences (S-ODN-5, oligo-dA, and oligo-dC) were also of interest. S-ODN-5, which does not exist in HIV either as an anti-sense or sense sequence, has the same content as dA, dG, dC, and dT residues and S-ODN-1, but is otherwise irrelevant to S-ODN-1. Oligo-dA and oligo-dC were used with 5, 14, and 28 nucleotide units to study the effects of chain length.

As defined herein, an anti-sense base sequence is a sequence complementary to the target genetic message which can serve to selectively suppress gene expression.

With regard to inhibition of cell proliferation, promyelocytic leukemia cells contain amplified copies of the c-mVc gene, a gene that is representative of a class of genes known as oncogenes, i.e., cellular genes whose de-regulation is involved in tumorigenesis.

Figure 3A:
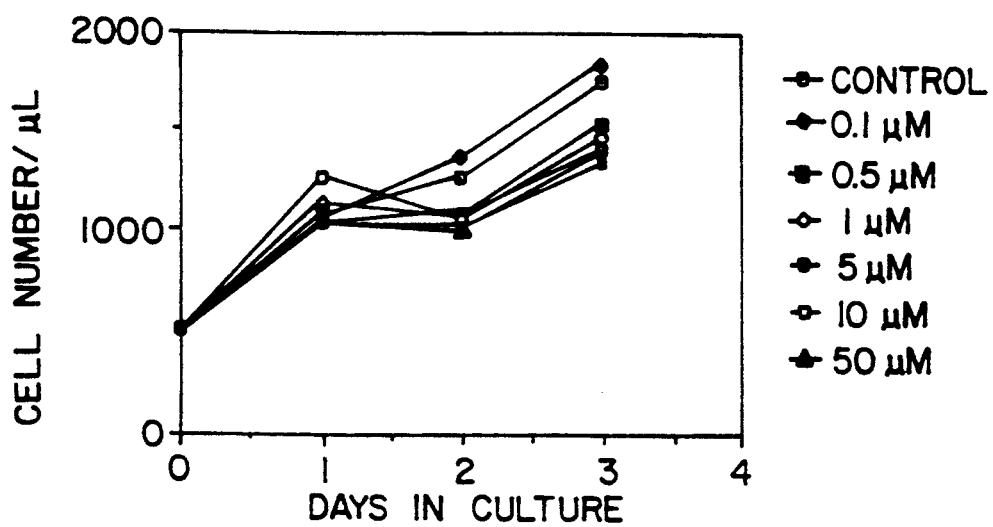
FIGS. 3A-3B show the effect of S-AS on HL60 cell growth.
Figure 3B:
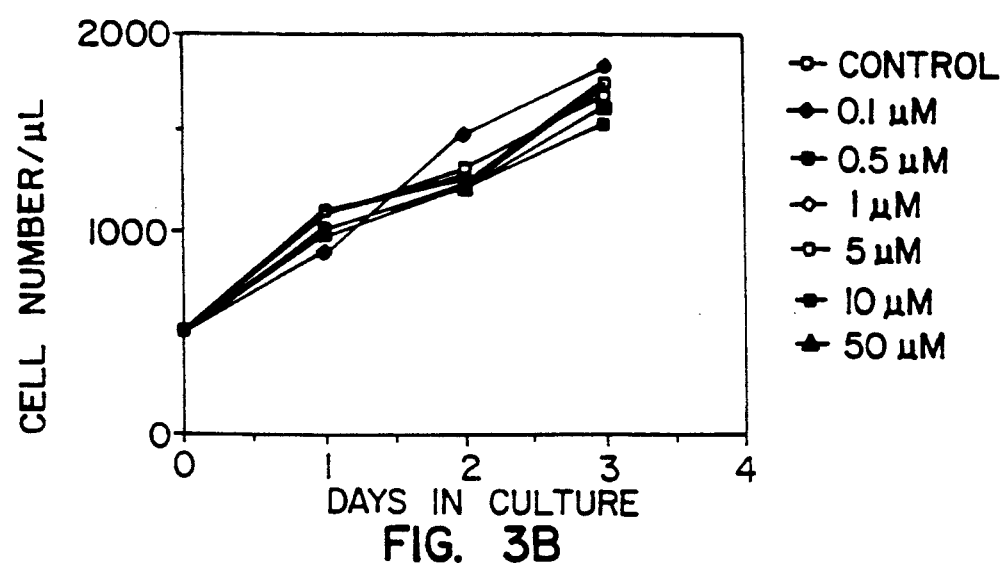
Figure 4:
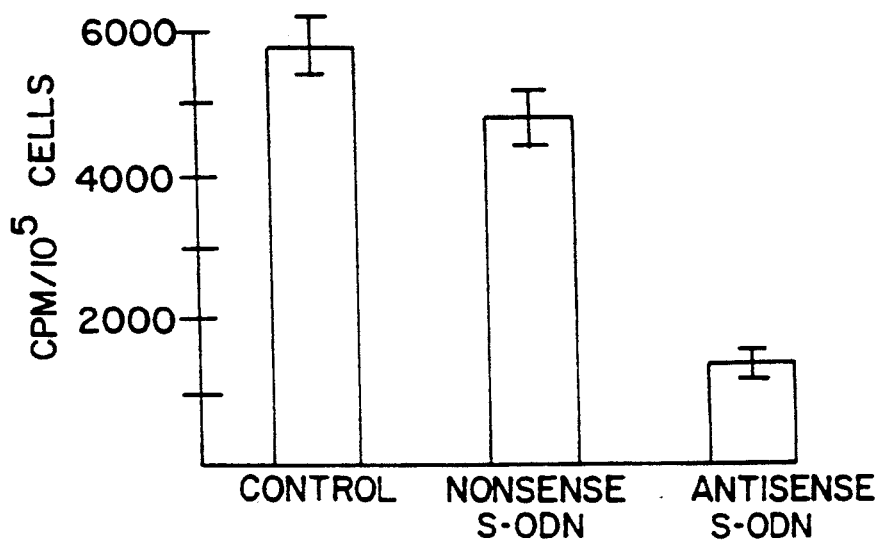
FIG. 4 shows the effect of S-AS ODNs inhibition of DNA synthesis in HL60 cells.

In the process according to the present invention, phosphorothioate oligodeoxynucleotide analogs of the same anti-sense sequence as previously described (i.e., complementary to the initiation codon of the c-myc gene) were found to inhibit proliferation of HL60 cells, cf. FIGS. 3 and 4.

It was found that only the anti-sense sequence provided significant inhibition of cell proliferation as measured by cell count, as shown in FIG. 3. and 3H-thymidine incorporation as shown in FIG. 4, as well as reduction of c-myc protein. The effects lasted for up to three days, using phosphorothioate oligodexoynucleotide concentrations significantly lower (i.e., less than 1%) than those required for the normal oligomer to have any real effect.

FIG. 3 shows antisense (top panel) and nonsense (bottom panel) sequences which were added on day 0 of cell culture to triplicated wells of a 96-well microtiter plate, and cell numbers were determined daily in all cultures. Antisense S-ODNs effectively inhibited growth of final concentrations between 0.5 and 10 microliters. While 0.1 micro M concentration of coantisense was effective, not all nonsense S-ODN concentrations affected cell proliferation.

To obtain the results shown in FIG. 4, nonsense or antisense S-ODNs were added at a final concentration of 50 uM on day 0 to cells seeded at $3 \times 10^5$/ml. DNA synthesis was determined on day 1 by incubating cells with 1 uCi 3H-thymidine for 4 hours, after which time 10% trichloroacetic acid was added and acid precipitable radioactivity was trapped on Whatman glass fiber filters. The filters were subjected to liquid scintillation counting to determine levels of radioactivity.

The effect has been reproduced three times, and none of the controls used, namely, the non-sense sequence, has shown similar activity. Thus, the inhibition of proliferation observed is unique to the specific ODN analog of the precise base sequence herein described. The use of this compound in vivo could result in the cessation of growth of a tumor whose proliferation is dependent on the presence of the c-myc gene. By extrapolation, the S-odn's complementary to sequences of other oncogenes will inhibit the growth of tumors in which these oncogenes are expressed.

TABLE 1 contains a list of the compounds which were synthesized for the antiviral tests. Each of the compounds was given a trivial name for the convenience of discussion, and has the molecular structure indicated by the conventional nomenclature for polynucleotides, with the exception that each internucleotide linkage indicated by subscript "s" is an Rp, Sp-phosphorothioate, wherein the average sulfur content is >95%, as judged by 31P NMR analysis.

It was found that longer oligos had more potent effects, and that oligo-dC phosphorothioate had more potency than oligo-dA phosphorothioate on the basis of molarity of the compounds. Therefore, the binding of the oligos to the relevant polynucleotide site(s) and/or the HIV reverse transcriptase (as primer) of the virus leads to protection against the cytopathic effects of HIV.

TABLE 1

Representative Test Compounds

| Trivial Name | Sequence (5'-3') of Phosphorothioate Analogues of Oligodeoxyribonucleotides |
|---|---|
| S-ODN-1 | d-($T_sC_sG_sT_sC_sG_sC_sT_sG_sT_sC_sT_sC_sC$) |
| S-ODN-2 | d-($G_sG_sA_sG_sA_sC_sA_sG_sC_sG_sA_sC_sG_sA$) |
| S-ODN-4 | d-($C_sA_sT_sA_sG_sG_sA_sG_sA_sT_sG_sC_sC_sT$) |
| S-ODN-4 | d-($C_sT_sG_sG_sT_sT_sC_sG_sT_sC_sT_sC_sC_sC$) |
| Oligo-dc | (dC)n  n = 5, 14, 28 |
| Oligo-dA | (dA)n  n = 5, 14, 28 |

S-ODN (phosphorothioate analogue-d) = oligodeoxy — nucleotides or phosphorothioates wherein dA and dC are compounds of Formula I.

Figure 1B:
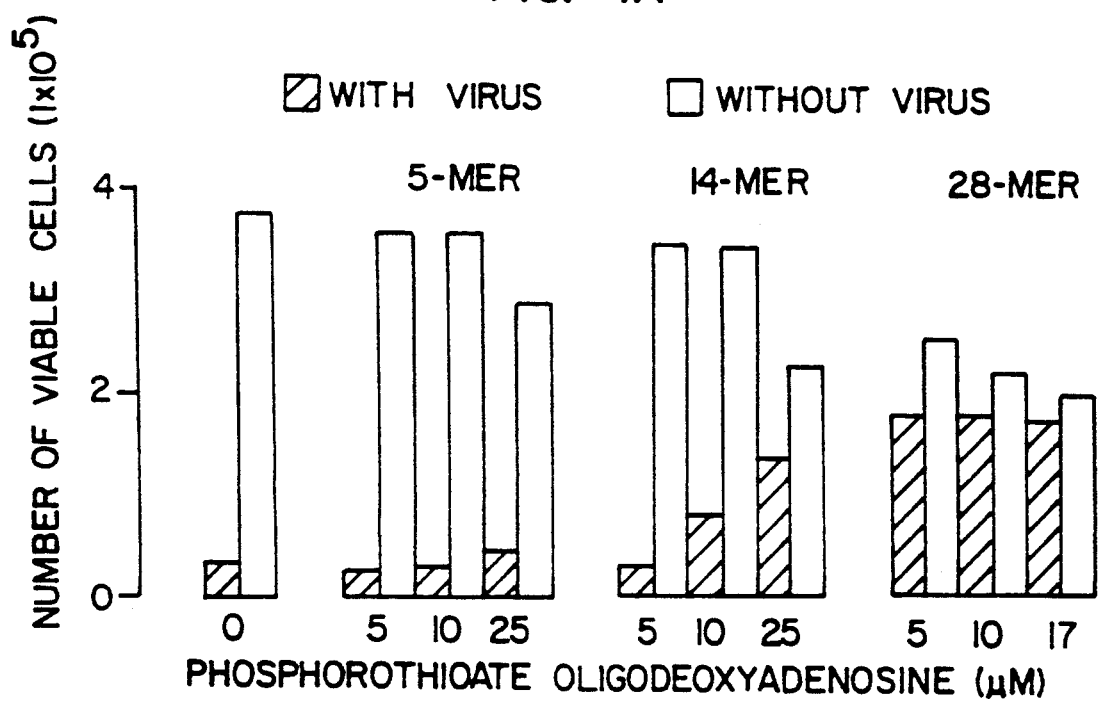
Figure 2A:
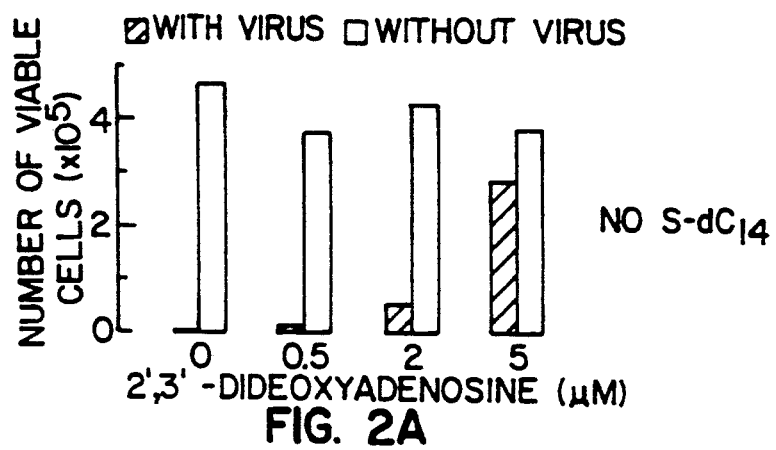
FIGS. 2A-2B show the effect of the combination of 2',3'-dideoxyadenosine and S-dC14.
Figure 2B:
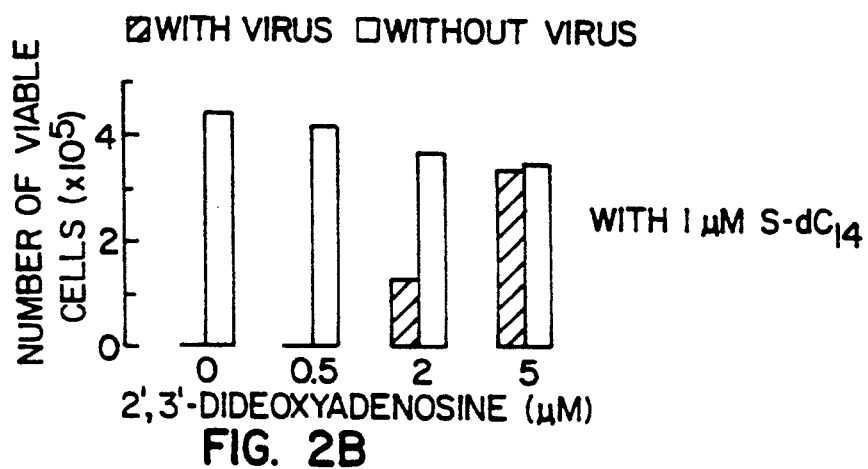
Figure 2C:
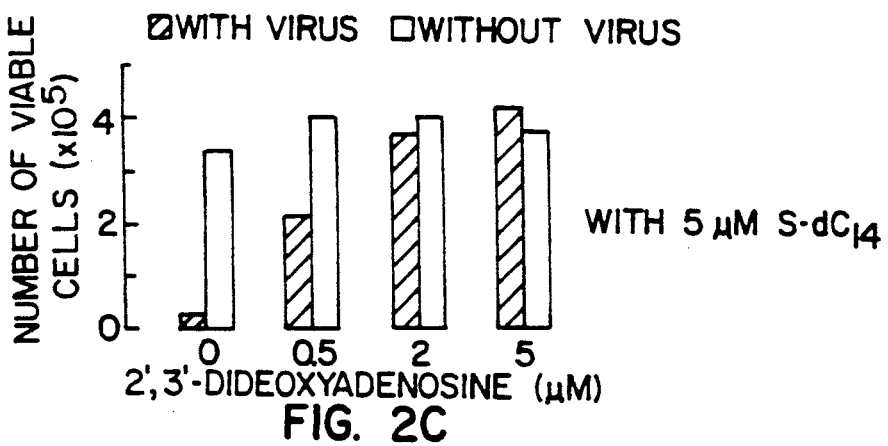
Figure 2D:
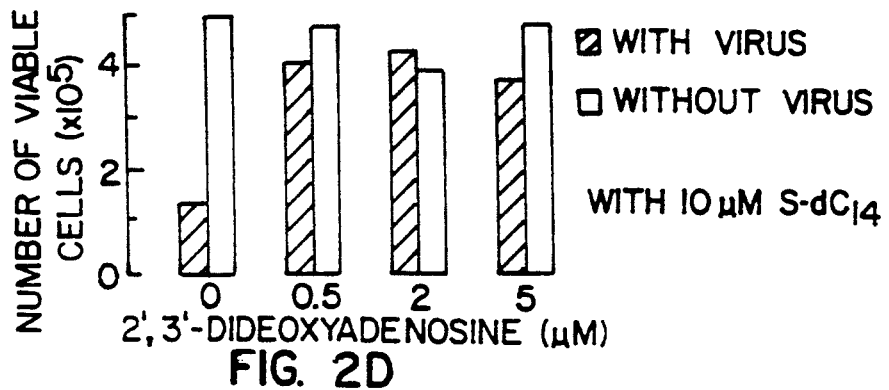

FIG. 1 shows a comparison of anti-HIV activity in three lengths of oligo-dC-S and oligo-dA-S. Oligo dC-phosphothioate 28 mer was found to inhibit viral replication and protect ATH8 cells from HIV to 100% at a concentration of 3 micromoles, cf. FIG. 1 and Table 1. The target cells ($2 \times 10^5$ ATH8 cells) in each tube were pre-treated with the stated concentration of each oligomer for 16 hours and then incubated with Polybrene for 45 minutes. After centrifugation, each set of pelleted cells was exposed to HIV (500 virions per cell, which is a much higher dose than the minimal cytopathic dose) and incubated for one hour. Complete media (2 ml RPMI1640) supplemented with L-glutamine (4 mM), 2-mercaptoethanol ($5 \times 10$-2M), penicillin (50 unit/ml), and streptomycin (50 micrograms/ml), and containing 15% fetal calf serum and IL-2 (15% of conventional IL-2 from Advanced Biotechnologies, Inc., Silver Spring, Md., plus 20 unit/ml of recombinant IL-2 from Amgen Biochemicals, Thousand Oaks, Calif.) with the various concentrations of oligomers added. The number of viable cells were counted in a hemocytometer using the trypan blue exclusion method for day 7 following exposure to the virus. Filled columns represent nonvirus exposed cells, and dotted columns represent virus exposed cells.

There are several possible mechanisms of the antiviral activity of the oligos, such as the inhibition of reverse transcriptase or direct effects against viral particles. Experiments using an assay for reverse transcriptase activity did not show significant inhibition of the enzyme activity.

The phosphorothioates of the present invention can be used with any pharmaceutically acceptable carriers such as, for example, water, saline solution, human blood, and other acceptable carriers.

HIV Culture with Olidodexoynucleotides

The HIV cytopathic effect inhibition with oligodeoxynucleotides was performed with 18 hours of pretreatment of $2 \times 10^5$ target cells (ATH8 cells) with oligos prior to exposure to HTLV-III$_B$. After this pretreatment, target cells were treated with Polybrene (2 micrograms/ml) for one hour. The target cells were then, respectively, exposed to HTLV-IIIB virus (generally 500 virions per cell in this series of experiments) for one hour. The $2 \times 10^5$ cells were then diluted to 2 ml with complete media containing IL-2 and various concentrations of oligos.

The number of viable cells was counted in a hemocytometer using the trypan blue exclusion method on day 7 following exposure to the virus. Each set of data were obtained from simultaneously performed experiments so as to make a precise comparison among agents tested.

Determination of HIV gag Protein Expression

The percentage of cells expressing p24 gag protein of HIV was determined by indirect immunofluorescence microscopy by using anti-HIV p24 murine monoclonal antibody.

Southern Blot Analysis

Target cells ($1 \times 10^7$ ATH8 cells) were pretreated with or without S-dC28 at various concentrations for sixteen hours, then treated with Polynrene, exposed to HIV (500 virus particles per cell), resuspended, and cultured in the presence or absence of S-dC28. On days 4 and 7 following the exposure to the virus, high molecular weight DNA was extracted, digested with Asp718 (a Kpn I isoschizomer from Boehringer-Mannheim, Indianapolis, Ind.), and subjected to Southern blot analysis hybridized with a labelled insert of molecular clone of the env region of HTLV-III (BH10) containing a 1.3 Kb Bgl II fragment.

The results of the antiviral effect and cytotoxicity of ODNS are shown in Table 2. The two n-ODNs and one M-ODN tested showed no significant inhibitory effects, while all the S-ODNs exhibited significant inhibition of the cytopathic effect of HIV. Surprisingly, the 14-mer phosphorothioate homo-oligomer of dC(S-dC14) was found to be the most potent antiviral compound among those tested in this series of experiments. Since phosphorothioate ODNs which are not anti-sense sequences appear to be very effective antiviral agents, an attempt was made to clarify the nature of the base composition effect. Comparing the effects of 5 micromoles of each of the 14-mer phosphorothioates tested, it was found that inhibition of the viral cytopathic effect was approximately linear with respect to the G+C content of the analog (cf. data from Table 2).

TABLE 2

| COM-POUND | ANTI-VIRAL EFFECT (%)[a] | | | | | CYTOTOXICITY (%)[b] | | | | |
|---|---|---|---|---|---|---|---|---|---|---|
| | 1 | 5 | 10 | 25 | (uM) | 1 | 5 | 10 | 25 | (uM) |
| S-ODN-1[c] | 0 | 43 | 72 | 95 | | 0 | 0 | 0 | 20 | |
| n-ODN-1[d] | 3 | 2 | 9 | 4 | | 35 | 22 | 27 | 14 | |
| M-ODN-1[e] | 8 | 20 | 13 | 10 | | 20 | 27 | 20 | 20 | |
| S-ODN-2 | 11 | 56 | 100 | 78 | | 0 | 0 | 0 | 6 | |
| n-ODN-2 | 11 | 9 | 0 | 11 | | 18 | 28 | 35 | 32 | |
| S-ODN-3 | 0 | 6 | 44 | 94 | | 0 | 0 | 0 | 13 | |
| S-ODN-4 | 0 | 53 | 78 | 100 | | 0 | 0 | 0 | 0 | |
| S-$^{dC}$14 | 25 | 100 | 100 | 100 | | 0 | 0 | 0 | 0 | |

Comparison of Anti-HIV Activity in Various Lengths of Oligo-dC and Oligo-dA Phosphorothioates Because it is possible that inter-assay variation may create an inappropriate comparison of antiviral activity among agents, experiments were performed simultaneously to make more precise comparisons.

FIG. 1 compares the anti-HIV activity of three lenths of S-dCs and S-dAs. The filled columns represent virus exposed cells. The inhibitory effects of S-dCn are greater and more persistent than those of S-dAn for 14-mer and 28-mer. The longer sequences were found to be more effective than the shorter ones.

In the comparison in FIG. 6 of the anti-HIV activity between the 14-mer and the 28-mer, it was found that there is obvious length effect even with an increase of several nucleotide lengths as short as three nucleotides.

As illustrated in FIG. 1, the inhibitory effects of S-dCn are greater and more persistent than those of S-dAn for both 14-m34 and 28-mer, while 5-mers belonging to both categories failed to inhibit the cytopathic effect of the virus significantly. The order of effectiveness of the homo-oligomers was dC>dT>dA for 14-mer. It was found that the longer sequences were more effective than the shorter sequences at the same molar concentration of nucleotide unit. For example, as shown in FIG. 6, the 28-mer S-dC28 at concentrations as low as 0.5 Micromoles (13.5 micromoles of nucleotide equivalents) gave complete protection against the virus, while the corresponding 14-m34 at 5 micromoles (65 micromole equivalents) had only a moderate effect. The S-dC28 gave the most consistent and durable antiviral effects under the conditions used in these experiments. These data suggest a real length effect, and argue against either metal ion chelation or degradation to reactive monomers.

Figures 5A, 5B:
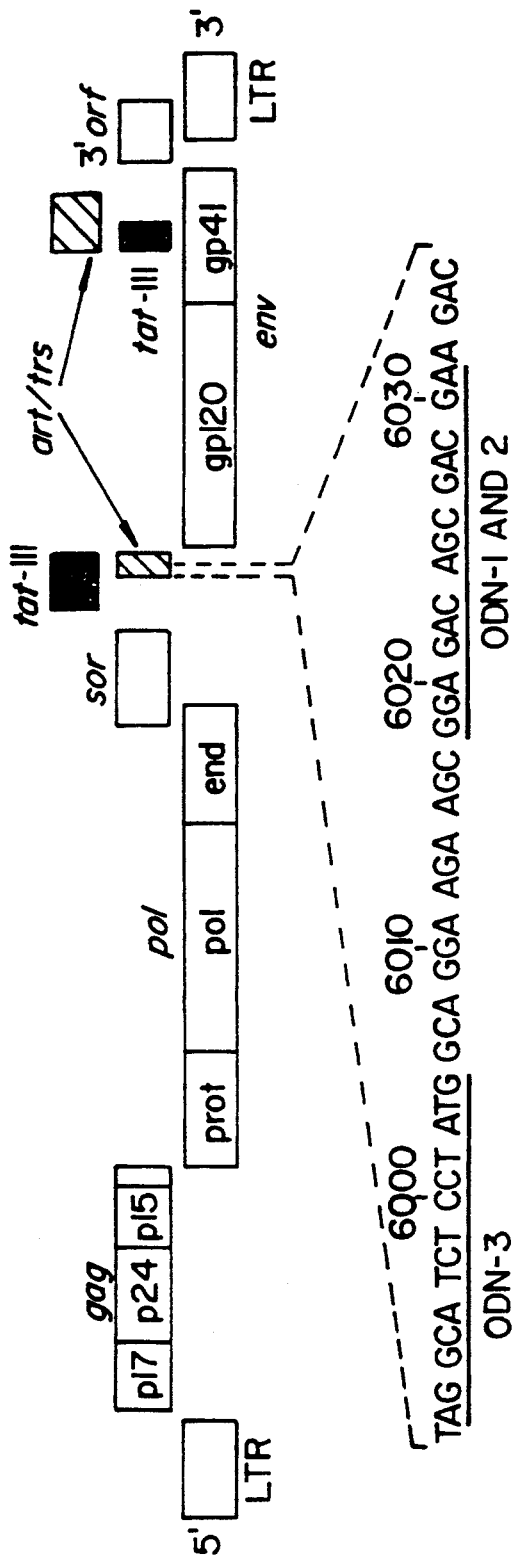
FIGS. 5A-5B show the DNA sequence of coding exon of art/trs gene in HTLV-III BH10 and the sequences of oligodeoxynucleotides tested.
Figure 6A:
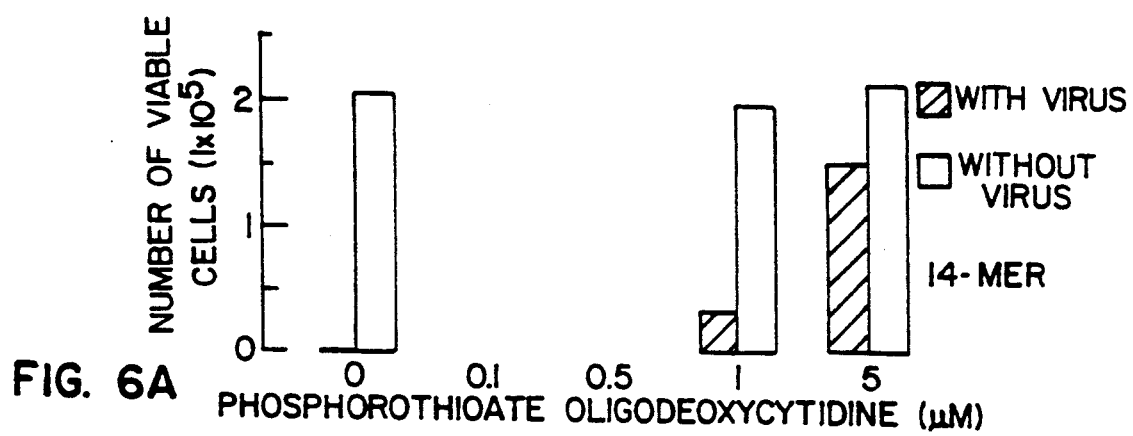
FIGS. 6A-6B shows a detailed comparison of anti-HIV activity between 14-mer and 28-mer of S-dCn.
Figure 6B:
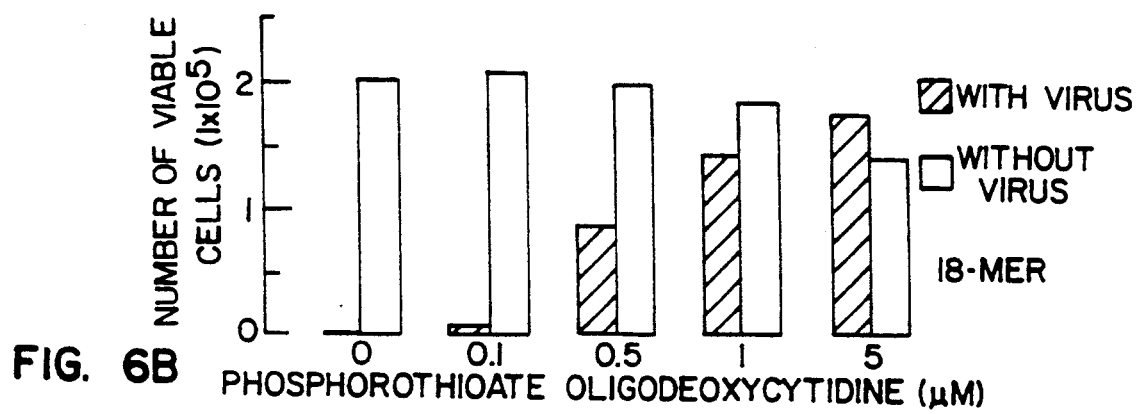
Figure 6C:
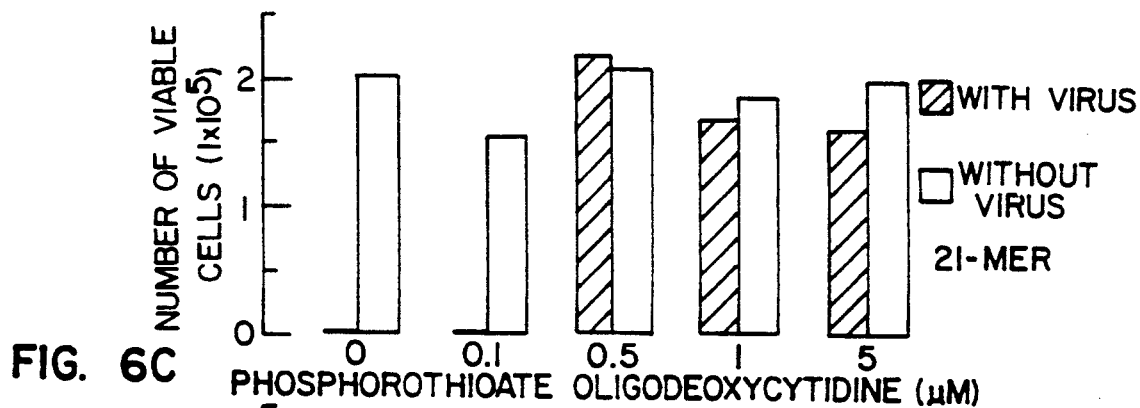
Figure 6D:
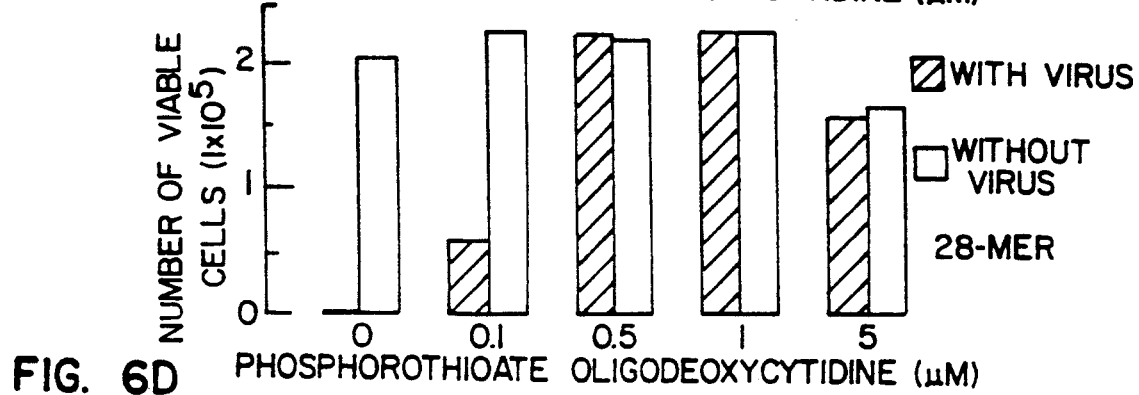

Effect of N3-methyl-thymidine Substitution in ODN Analog on Anti-HIV Activity In FIG. 5, N-Me-ODN-1 of N3-methyl-thymidine-containing anti-sense oligodeoxynucleotide, which has a methylated thymidine at positions 4 and 9. Random sequence ODN-4 has the same base content as ODN-1, but has less than 70% homology with any sequence in HTLV-III BH10 genomic sequence as anti-sense or as sense. The homo-oligomer of dC and dA were synthesized in three lengths, where n was 5, 14, and 28.

Figure 7A:
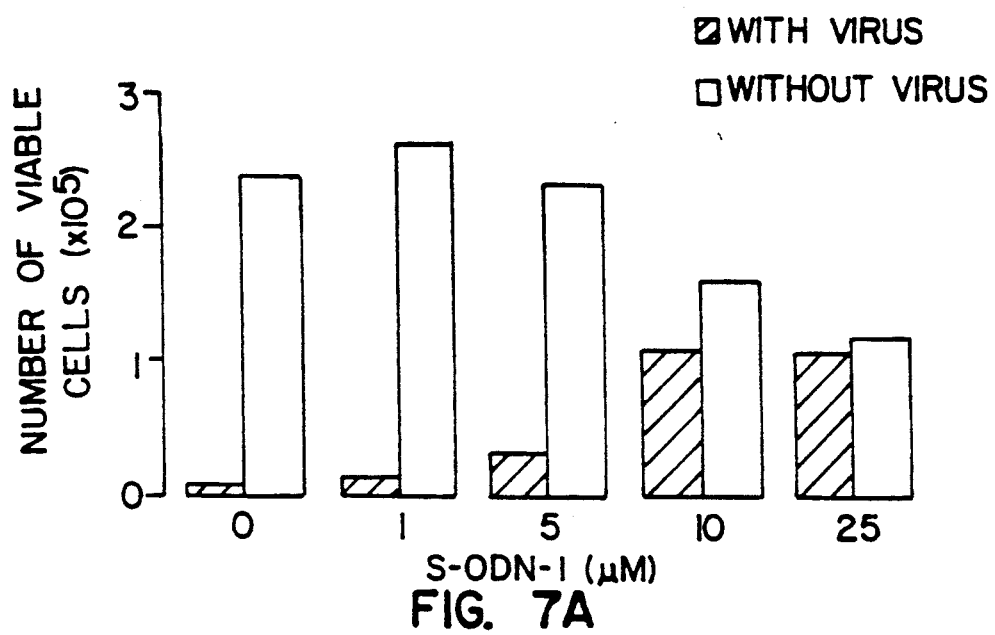
FIGS. 7A-7B show the effect of N-methylation of thymine on the antiviral activity of S-ODN-1.
Figure 7B:
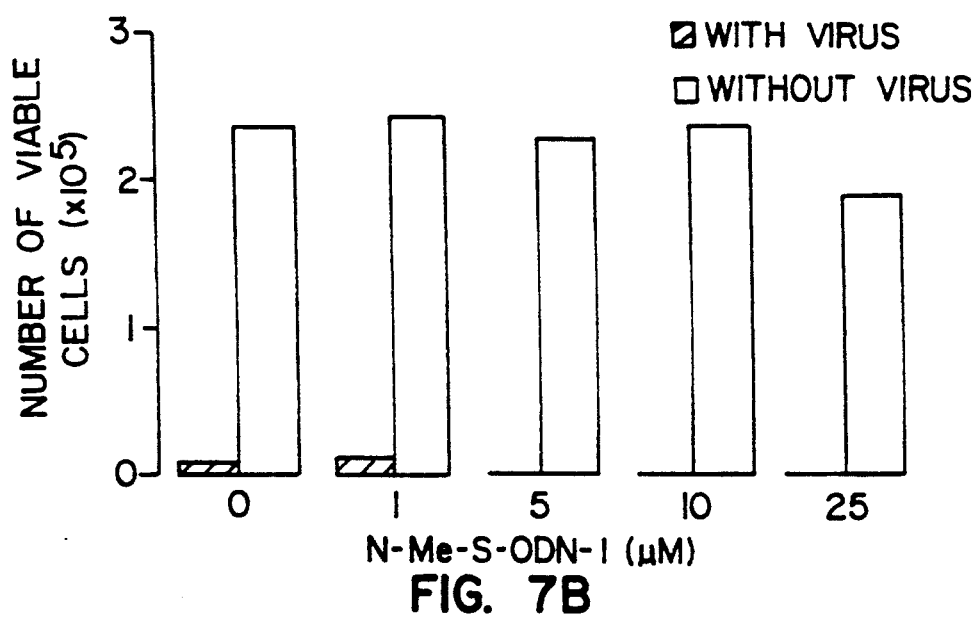

N3-methyl-thymidine-containing S-ODN-1 showed no anti-HIV activity, while S-ODN-1 consistently exhibited substantial activity against HIV, as shown in FIG. 7. Since N3-substitution on the pyrimidine base is known to reduce hydrogen bonding profoundly to complementary adenosine residues, the relative inactivity of this N3-methyl-thymine-containing analog of phosphorothioate suggests that antiviral activity could be brought about by binding to nucleotide sequences at least one mechanism.

Inhibition of de novo HIV DNA Synthesis in ATH8 Cells Exposed to the Virus by 28-mer of Oligodeoxycytidine Phosphorothioate FIG. 6 shows the inhibitor effect of the phosphorothioate oligodeoxycytidine analog (S-dC28) on de novo HIV DNA synthesis in target cells. On days 4 and 7 following the exposure to the virus, a substantial amount of viral DNA was detected by Southern blot analysis without antiviral agents. S-dC28, as well as 2',3'-dideoxyadenosine as the positive control, significantly inhibited the de novo synthesis of viral DNA at concentrations as low as 1 micromolar.

On day 4, shown in lanes A-E, and day 7, shown in lanes F-J, following exposure to the virus, high molecular weight DNA was extracted. Lanes A and F contain DNA from ATH8 cells that were exposed to the virus and not protected by S-dC28. Lanes B and G, C and H, D and I, contain DNA from ATH8 cells pretreated and cultured with 1 micromole, 5 micromoles, and 7 micromoles S-dC28, respectively. Lanes E and J contain DNA from ATH8 cells treated with 50 micromoles 2',3'-dideoxyadenonsine, and lane K contains DNA from ATH8 cells that was not exposed to the virus. The 2.7 Kb env-containing internal KPN I fragment of the virus genome was detected only in lanes A and F.

Failure to Inhibit the Expression of Viral Protein by 28-mer Oligodeoxycytidine Phosphorothioate (S-dC28) in Chronically HIV infected Cells As illustrated in Table 3, S-dC28 failed to reduce gag protein positivity of target cells assessed by indirect immunofluorescent assay in chronically HIV-infected H9 cells at concentrations as high as 25 micromoles for the duration of the experiment, 120 hours.

TABLE 3

| Percentage of gag positive cells | | | | |
|---|---|---|---|---|
| S-$dC_{28}$ | 8 | 24 | 72 | 120 |
| | (hours in Culture with Compound) | | | |
| 0 micro M | 79 | 90 | 70 | 78 |
| 5 micro M | 82 | 91 | 85 | 79 |
| 10 micro M | 74 | 80 | 71 | 82 |
| 25 micro M | 69 | 86 | 75 | 74 |

Synergistic Enhancement of Antiviral Activity of 2',3'-Dideoxyadenosine by 14-mer Oligodeoxycytidine Phosphorotioate It is emphasized that the various dideoxynucleosides, including azidothymidine (AZT), dideoxycytidine, and dideoxyadenosine, require anabolic phosphorylation within target cells to become active anti-retroviral agents. The mechanisms of action appear to be competitive inhibition of reverse transcriptase and/or termination of nascent DNA chain formation FIG. 2 shows the effect of the combination of 2',3'-dideoxyadenosine and S-dC14. Synergistic effects were obtained with a combination of S-dC28 or S-dC14 and a dideoxynucleoside. The target cells (2 × 105 ATH8 cells per tube) were preincubated with the stated concentrations of S-dC14 for 24 hours and pretreated with 2 micrograms/ml of Polybrene for 45 minutes. After centrifugation, pelleted cells were exposed to the HIV (1000 virions per cell) for one hour. The cells were incubated in 2 ml of complete media containing IL-2, and the viable cells were counted on day 13.

The oligomers of the present invention are likely to work by different mechanisms and would not be expected to require anabolic phosphorylation. However, as shown in FIG. 7, the combination of 2',3'-dideoxyadenosine and 14-mer oligodeoxycytidine phosphorothioate gave a marked synergistic enhancement of antiviral activity. For example, 2 micromoles of dideoxyadenosine showed complete protection of target cells against the viral cytopathic effect with 5 exclusion method. These experiments involved a more potent viral inoculum for a longer duration than in the other experiments described herein.

As shown in Table 2, only phosphorothioate analogs showed anti-HIV activity. Thus, it is believed that it is mainly the relative resistance of the phosphorothioate analogs to nucleases that preserves them relative to n-ODNs, and allows them to reach and remain at their target site. This was supported in relation to the media used in the in vitro test system by following the 31P NMR spectra of the n-ODN-1 and S-ODN-1 compounds as a function of time. Breakdown of the normal oligodeoxynucleotide was seen from the buildup of the terminal phosphate peak, indicating a half-life of about seventeen hours under these conditions, while the S-analogs exhibited no significant degradation even after a week, within the greater than 5% accuracy of the method.

Similarly, samples of solution of S-ODNs taken from the in vitro cytopathic assay and incubated in human serum at 37° C. showed no degradation after seven days. The inactivity of a methylphosphonate analog (M-ODN-1) in the cytopathic inhibition assay could have been due to its poor ability to hybridize strongly to the target sequence.

The potency of Anti-HIV activity of S-dC28, one of the most potent analogs tested, is almost comparable to that of 2',3'-dideoxycytidine on the basis of molarity, i.e. both agents showed complete antiviral activity at 0.5 micromoles in the present assay system, as well as in terms of therapeutic index, the ratio of cytotoxic concentration relative to effective concentration. S-dC28 generally shows a comparable in vitro index to those of dideoxycytidine and dideoxyadenosine.

Generally, it has been assumed that anti-sense sequences inhibit the expression of various genes by translation arrest, i.e. that they bind to mRNA and block its translation. In order to test this possibility, gag protein synthesis was analyzed in chronically HIV-infected and -producing H9 cells by indirect immunofluorescent assay under a microscope. S-dC28 did not inhibit gag protein positivity in H9/IIIb cells at concentrations as high as 25 micromoles, as shown in Table 3. Although gag positivity of cells is only a partially quantitative parameter for protein production, this result suggests that the potent anti-HIV activity of S-dC28 at concentrations as low a 0.5 micromoles might not be from a translation arrest per se. Alternatively, the level of any translation arrest could have been below the threshold of detection by indirect immunofluorescent assay under a microscope. By contrast, a Southern blot analysis used to explore de novo synthesis of HIV DNA in target cells showed complete inhibition by S-dC28 at concentration down to 1 micromole, as shown in FIG. 6. Therefore, one mechanism for the antiviral effect could depend on blocking viral replication perhaps prior to, or at the stage of, pro-viral DNA synthesis.

The possibility that the S-ODN analogs may interfere with HIV binding to target cells was tested. The T4 molecule on the cell surface is known to be the main receptor for HIV in T4+cells, No inhibition by S-dC28 was observed in experiments using radiolabelled virus for specific binding to the labelled virus to the T4 molecule in T4 cells (H9 cells), thus suggesting that inhibition of viral binding to the cell surface is not responsible for the activity. In addition, no detectable changes in the T4, HLA-DR, T8, T3, or Tac antigen on the cell surface of ATH8 cells were shown by fluorescent-activated cytofluorometry after sixteen hours of incubation with i micromole S-dC28. Overall, these findings, including a base composition effect and a length effect, as shown in Table 1 and FIG. 4, suggest that the antiviral activity is mediated by inhibition of HIV pro-viral DNA synthesis, perhaps brought about, at least in part, by binding of the S-ODNs to a viral nucleotide sequence.

Another mechanism which should be considered is induction of interferon production such as that proposed for phophorothioate analogs of poly-r(I-C). No induction of gamma-interferon was observed in the supernatant of the culture with S-dC14, and 1000 units of recombinant alpha- or gamma-interferon added directly to the cultures did not inhibit the cytopathic effect in the assay systems. Also, since there are no data to support the concept that phosphorothioate internucleotide linkages have a thiol character, and can thus form disulfides, the mechanism of action would likely be different from that proposed for antiviral polynucleotides having thiolated bases such as 5-mercaptocytosine or -uracil.

Phosphatase-resistant 35S-phosphorothioate end-labelled S-dC28 was employed to investigate the permeability of target cells. Significant increases of radioactivity in ATH8 and H9 cells were observed within several minutes, thus supporting the uptake of these compounds by the cells.

S-ODNs also showed substantial inhibition of purified HIV reversed transcriptase activity in the in vitro experiment using a viral DNA (3'-orf) inserted in an M-13 vector as a template with a universal primer. Under some conditions, it was found that phosphorothioate analogs can serve as competitive inhibitors of template-primer, and that this class of compounds appears to have multiple mechanisms of action. The precise mechanism, however, including non-sequence specificity of the antiviral activity, direct inhibition of the viral DNA polymerase or additional translation arrest at high concentration for complementary sequences, requires further research at this time.

After a number of days in culture, generally 7-10 days, either substantial cell death due to HIV infection (HIV cytopathic effect) or the protective effect of oligos against the cytopathicity of HIV was observed.

In other experiments, protection of the target cells (ATH8 cells) appeared to be protected against HIV by phosphorothioate oligos (S-ODN-1, 2, and 4), but not by unmodified oligos which have the same sequences. Moreover, in the same experiment, "random" sequences of phosphorothioate, such as the 14-mer oligo-dC and S-ODN-5, showed substantial protection against HIV cytopathic effect. The protective effects of the phosphorothioate oligos brought about by binding to relevant polynucleotide sites for infection and cytopathcie effects of the virus were also investigated, as well as various lengths of oligo-dC and oligo-dA phosphorothioates (5, 14, and 28 mers) in the cytopathic effect assay. Bio testing is described in Mitsuya et al., *PNAS*, 83: 1911-1915 (1986).

With respect to inhibition of tumor growth, the effects of the all-phosphoro oligomers are quite different from the effects of the all-phosphothioated oligomers. Additionally, combined mixtures of chemically combined copolymers of the oligomers of the present invention can be used to inhibit proliferation of tumor cells.

These copolymers can assume a variety of configurations, for example, an end-capped polymer with two phosphothionated oligomers at each end of a 14-mer polymer. Alternatively, block copolymers can be provided, such as polymers with repeating blocks such as nine phosphonate, nine phosphothionated, and nine phosphonated mers in a 28-mer polymer which has 27 internucleotide phosphate bonds, or singly alternating copolymers. Many of these copolymers have intermediate properties.

It has been found that the normal oligomers are cleaved after about seventeen hours in serum, but that in the cell, the half-life of these compounds may be as long as several days. The use of the phosphorothionated derivatives lengthens the lifespan of the active compounds, which provides these compounds more time in which to inhibit the expression of the oncogenes.

Initial physico-chemical studies indicate that the end-capped compounds are quite resistant to nucleases, by a factor of about 100, but hybridize almost as well as the normal phosphonated compounds, as indicated by their melting temperatures, as shown in Table 4, below.

TABLE 4

| Melting Temperature of Oligomers* | | | |
|---|---|---|---|
| With Poly-rA: | | | |
| O-dT7 | 10° C. | | |
| O-dT14 | 39 | S-dT14 | 20 |
| O-dT21 | 48 | | |
| S-dT28 | 52 | S-dT28 | 36 |
| S-dT15 | | 23 | |
| 2S-3',5' cap-dT15 | | 37 | |
| 4S-3',5' cap-dT21 | | 43 | |
| 5S-3',5' cap-dT23 | | 44 | |
| Homo-duplexes: | | | |
| S-dT14 + O-dA14 | | 21 | |
| S-dT28 + O-dA28 | | 39 | |
| O-dT14 + O-dA14 | | 38 | |
| S-dT28 + S-dA28 | | 32 | |
| LAS1 dGGGAAGGATGGCGACGCTG) (70% G/C): | | | |
| S-sense + S-antisense | | 56 | |
| S-sense + O-antisense | | 65 | |
| O-sense + O-antisense | | >75 | |

*Determined by UV melting at 260 nm.
NOTE:
S-dA/T Tms are quite low, but S-dC/G are relatively high!

Several oligodeoxynucleotides were studied with regard to DNase sensitivity, cf. Table 5. These include cytidine homopolymers, ODN-4 (an anti-message 38-mer complementary to the 3' region of the art/trs region of HIV BH10 clone), and myc-1 (a 15-mer complementary to the initiation codon region of the C-myc oncogene). The DNases employed were predominantly endonuclease S1, the exo- and endonuclease P1, and snake venom (SV) phosphodiesterase. The concentration of S1 nuclease was ten-fold higher (100 micromoles/ml) for reactions of olifo-dC, since both the normal and PS analog were degraded extremely slowly be this enzyme. S1 and P1 nuclease digestion proceeded at 2-45 times more slowly for the S-ODNs than for the normal oligomers, with the 150-mer being somewhat more readily digested than the 28-mer. The 2S-capped myc-1 species behaved similarly to the all-PS compounds.

The S-ODNs are all but impervious to the effects of SV phosphodiesterase, and in this case the differences from normal oligos are quite dramatic. For the homopolymers, a half-life of $>10^5$ seconds was determined, which represents a three-log decrease of the rate versus the normal oligomer. Similar results were found with myc-1 and ODN-4. Digestion of 2S-cap-myc-1 by SV phosphodiesterase was also slowed, as shown in Table 5, but not as markedly as some of the other species. However, the half-life of 3',5'-2S-cap-myc-1 in 50% human serum, as measured by 31P NMR, is greater than one month vs two to three days for normal myc-1.

TABLE 5

| Nuclease Susceptibilities of Oligomers, $t_{\frac{1}{2}}$ (sec)[1] | | | | | |
|---|---|---|---|---|---|
| O-dC$_{15}$ | 822 | | 1810 | | 35 | |
| S-dC$_{15}$ | 11000 | 134 | 27700 | 15.3 | 133000 | 3800 |
| O-dC$_{28}$ | 3910 | | 3160 | | 70 | |
| S-dC$_{28}$ | 7990 | 2 | 48600 | 15 | >100000 | >1400 |
| O-ODN-4 | 203 | | 72 | | 20 | |
| S-ODN-4 | 8370 | 41 | 1370 | 19 | 92500 | 4625 |
| O-myc-1 | 36 | | 69 | | 28 | |
| S-myc-1 | 330 | 9 | 249 | 4 | 12400 | 443 |
| myc-1-cap | 1530 | 43 | 807 | 12 | 4230 | 151 |

[1]Ratio = $t_{\frac{1}{2}}$PS-oligo/$t_{\frac{1}{2}}$PO-oligo
ODN-4 = d-TCGTCGCTGTCTCCGCTTCTTCCTGCCA
myc-1 = d-AACGTTGAGGGGCAT As described previously, the preferred dosage of the compounds of the present invention is that which is necessary to attain a concentration in blood of from about 0.1 to about 100 micromoles/cl. This concentration can be achieved in a variety of ways.

Pharmaceutical compositions within the scope of the present invention include compositions wherein the active ingredient thereof is contained in an effective amount to achieve its intended purpose. Although a preferred range has been described above, determination of the most effective amounts for treatment of each type of tumor or virus is within the skill of the art.

In addition to the phosphothioated compounds of the present invention, these pharmaceutical compositions may contain suitable excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and preparations which can be administered rectally, such as suppositories, as well as suitable solutions for administration parenterally or orally, and compositions which can be administered bucally or sublingually, including inclusion compounds, contain from about 0.1 to about 99 percent by weight of active ingredients, together with the excipient.

The pharmaceutical preparations of the present invention are manufactured in a manner which is itself well known in the art. For example, the pharmaceutical preparations may be made by means of conventional mixing, granulating, dragee-making, dissolving, or lyophilizing processes. The process to be used will depend ultimately on the physical properties of the active ingredient used.

Suitable excipients are, in particular, fillers such as sugars, for example, lactose or sucrose, mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl-starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate, and/or polyethylene glycol. Dragee cores may be provided with suitable coatings which, if desired, may be resistant to gastric juices. For this purpose, concentrated sugar solutions may be used, which may optionally contain gum arabic, talc, polyvinylpyrrolidone, polyethylene glycol, and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs and pigments may be added to the tablets of dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include, for example liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

Additionally, the compounds of the present invention may also be administered encapsulated in liposomes, pharmaceutical compositions wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomycelin, steroids such as cholesterol, more or less ionic surfactants such as dicetylphosphate, stearylamine, or phosphatidic acid, and/or other materials of a hydrophobic nature. The diameters of the liposomes generally range from about 15 nm to about 5 microns.

Another pharmaceutically acceptable carrier for the compounds according to the present invention are liposomes, pharmaceutical compositions in which the active ingredient is contained either dispersed or variously present in corpuscles consisting of aqueous concentric layers adherent to lipidic layers. The active ingredient may be presenbt both in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomycelin, steroids such as cholesterol, more or less ionic surface active substances such as dicetylphosphate, stearylamine or phosphatidic acid, and/or other materials of a hydrophobic nature.

The foregoing description of the specific embodiments will so fully reveal the general nature of the invention that other can, by applying current knowledge, readily modify and/or adapt for various applications such specific embodiments without departing from the generic concept, and therefore such adaptations and modifications are intended to be comprehended within the meaning and range of equivalents of the disclosed embodiment. It is to be understood that the phraseology or terminology employed herein is for the purpose of description and not of limitation.

What is claimed is:

1. A compound capable of inhibiting the replication or cytopathic effect of a foreign nucleic acid in a host of the formula:

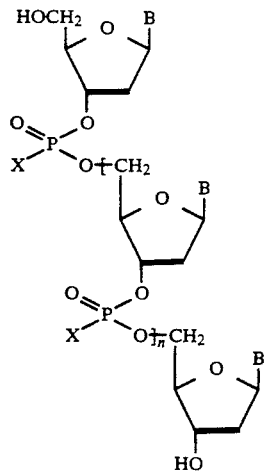

wherein:
n is in the range of from 2 to 30, inclusive;
X is selected from the group consisting of S and O such that at least one X is S; and B is selected from the group consisting of adenine, cytosine, guanine, and thymine, such that the compound has a complementary base sequence with a portion of the foreign nucleic acid.

2. The compound of claim 1 wherein n is in the range of from 14 to 30, inclusive.

3. The compound of claim 2 wherein greater than 95% of X are S.

4. The compound of claim 3 wherein X is S.

5. The compound of claim 2 wherein two X are S and the remaining X are O.

6. The compound of claim 5 wherein the two X which are S are at opposite terminal ends of the compound with respect to one another.

7. The compound of claim 2 wherein the number of X which are S is equal to the number of X which are O.

8. The compound of claim 2 wherein the X are grouped in alternating units, said alternating units being, respectively, units in which all X are S and units in which all X are O, and further wherein the number of X in each unit is equal.

9. The compound of claim 8 wherein the number of X in each unit is one.

10. The compound of claim 1 wherein said foreign nucleic acid is a viral nucleic acid.

11. The compound of claim 10 wherein n is in the range of from 14 to 30, inclusive.

12. The compound of claim 11 wherein said viral nucleic acid is a nucleic acid of human immunodeficiency virus.

13. The compound of claim 12 wherein said nucleic acid of human immunodeficiency virus is a gag gene nucleic acid.

14. The compound of claim 12 wherein said nucleic acid of human immunodeficiency virus is a tat-III gene nucleic acid.

15. The compound of claim 12 wherein said nucleic acid of human immunodeficiency virus is an art/trs gene nucleic acid.

16. The compound of claim 11 wherein greater than 95% of X are S.

17. The compound of claim 16 wherein X is S.

18. The compound of claim 16 wherein said viral nucleic acid is a nucleic acid of human immunodeficiency virus.

19. The compound of claim 18 wherein X is S.

20. The compound of claim 18 wherein said nucleic acid of human immunodeficiency virus is a gag gene nucleic acid.

21. The compound of claim 18 wherein said nucleic acid of human immunodeficiency virus is a tat-III gene nucleic acid.

22. The compound of claim 18 wherein said nucleic acid of human immunodeficiency virus is an art/trs gene nucleic acid.

23. A composition for inhibiting the replication or cytopathic effect of a foreign nucleic acid in a host, said composition comprising a pharmaceutically acceptable carrier and an effective amount of a compound of the formula:

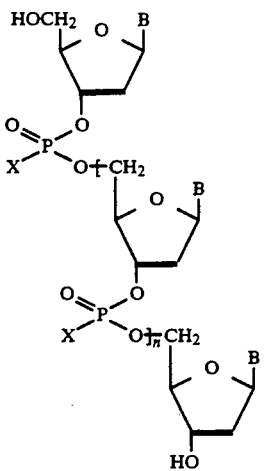

wherein:
n is in the range of from 2 to 30, inclusive;
X is selected from the group consisting of S and O such that at least one X is S; and
B is selected from the group consisting of adenine, cytosine, guanine, and thymine, such that the compound has a complementary base sequence with a portion of the foreign nucleic acid.

24. The composition of claim 23 wherein n is in the range of from 14 to 30, inclusive.

25. The composition of claim 24 wherein greater than 95% of X are S.

26. The composition of claim 25 wherein X is S.

27. The composition of claim 23 wherein said foreign nucleic acid is a viral nucleic acid.

28. The composition of claim 27 wherein n is in the range of from 14 to 30, inclusive.

29. The composition of claim 28 wherein said viral nucleic acid is a nucleic acid of human immunodeficiency virus.

30. The composition of claim 29 wherein said nucleic acid of human immunodeficiency virus is a gag gene nucleic acid.

31. The composition of claim 29 wherein said nucleic acid of human immunodeficiency virus is a tat-III gene nucleic acid.

32. The composition of claim 24 wherein said nucleic acid of human immunodeficiency virus is an art/trs gene nucleic acid.

33. The composition of claim 29 wherein greater than 95% of X are S.

34. The composition of claim 33 wherein X is S.

35. A method for inhibiting the replication or cytopathic effect of a foreign nucleic acid in a host comprising the step of administering to the individual an effective amount of a compound of the formula:

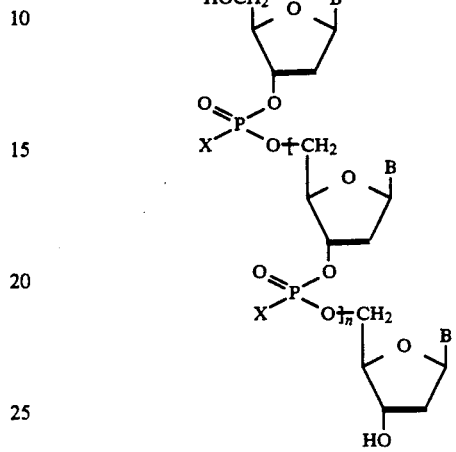

wherein:
n is in the range of from 2 to 30, inclusive;
X is selected from the group consisting of S and O such that at least one X is S; and
B is selected from the group consisting of adenine, cytosine, guanine, and thymine, such that the compound has a complementary base sequence with a portion of the foreign nucleic acid.

36. The method of claim 35 wherein n is in the range of from 14 to 30, inclusive.

37. The method of claim 36 wherein greater than 95% of X are S.

38. The method of claim 37 wherein X is S.

39. The method of claim 35 wherein said foreign nucleic acid is a viral nucleic acid.

40. The method of claim 39 wherein n is in the range of from 14 to 30, inclusive.

41. The method of claim 40 wherein said viral nucleic acid is a nucleic acid of human immunodeficiency virus.

42. The method of claim 41 wherein greater than 95% of X are S.

43. The method of claim 42 wherein X is S.

* * * * *

UNITED STATES PATENT AND TRADEMARK OFFICE
Certificate

Patent No. 5,276,019　　　　　　　　　　　　　　　　　　　　　　　Patented: January 4, 1994

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jack S. Cohen, Bethesda, MD; Gerald Zon, San Carlos, CA; Makoto Matsukura, Kumamoto City, Japan; and Kazuo Shinozuka, Kazo, Japan.

Signed and Sealed this Eighth Day of April 2003.

MARIAN C. KNODE
　　　　　　　　　　　　　　　　　　　　　　　　　　　　　*Supervisory Patent Examiner*
　　　　　　　　　　　　　　　　　　　　　　　　　　　　　　　　　　Art Unit 1800